United States Patent [19]

Nagakura et al.

[11] 3,970,593
[45] July 20, 1976

[54] TRICYCLIC HYDROCARBON AND PROCESS FOR PRODUCING THE SAME

[75] Inventors: Akira Nagakura, Kawaguchi; Susumu Akutagawa, Yokohama; Haruki Kurihara, Tokyo, all of Japan

[73] Assignee: Takasago Perfumery Co., Ltd., Tokyo, Japan

[22] Filed: Dec. 27, 1974

[21] Appl. No.: 537,039

[30] Foreign Application Priority Data

Jan. 11, 1974 Japan................................. 49-6388

[52] U.S. Cl............................. 252/522; 260/348 C; 260/666 A; 260/586 R
[51] Int. Cl.².................................... C07D 303/06
[58] Field of Search................. 260/348 C; 252/522

[56] References Cited
UNITED STATES PATENTS 2,838,524  6/1958  Wilson ............................. 260/348.5
3,671,551  6/1972  Bledsoe............................. 252/522

*Primary Examiner*—Norma S. Milestone
*Attorney, Agent, or Firm*—Sughrue, Rothwell, Mion, Zinn & Macpeak

[57] ABSTRACT

5,6-Epoxy-1,2,6-trimethyltricyclo[5,3,2,0$^{2,7}$]dodecane having the formula (I)

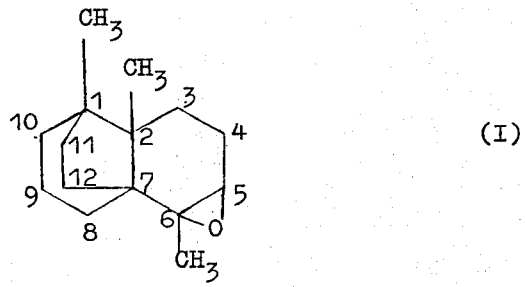

(I)

and a process for producing this compound. This compound is useful as a perfume.

2 Claims, 4 Drawing Figures

TRICYCLIC HYDROCARBON AND PROCESS FOR PRODUCING THE SAME

BACKGROUND OF THE INVENTION

1. Field of the Invention

This invention relates to a tricyclic hydrocarbon, 5,6-epoxy-1,2,6-trimethyltricyclo[5,3,2,0^{2,7}]dodecane and to a process for producing this compound.

2. Description Of The Prior Art

Amber-like fragrant substances are important starting materials for a blended perfume, and, of these substances, ambergris obtainable from sperm whales is the most expensive. The fragrance component of ambergris was clarified by E. Lederer and L. Ruzicka in 1946 to be a substance formed from ambrein which is a triterpene compound. Ever since, many attempts to synthesize amber-like fragrant substances equal to the natural material, or similar substances, have been made. Some of them can be utilized as a substitute for expensive ambergris. For example, manool derivatives, which are diterepene compounds and can be obtained from a special needle-leaf tree, are widely used as such a substitute. However, in general, amber-like fragrant substances are difficult to synthesize and moreover, special natural products are required as a starting material to synthesize amber-like fragrant substances. Therefore, synthetic amber-like fragrant substances are inevitably expensive.

SUMMARY OF THE INVENTION

This invention provides 5,6-epoxy-1,2,6-trimethyl-tricyclo-[5,3,2,0^{2,7}]dodecane having the formula

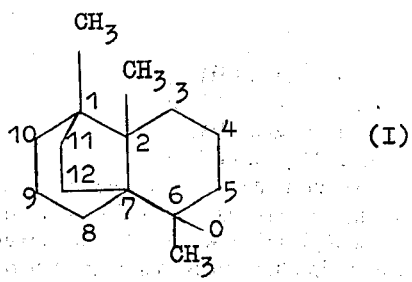

and a process for producing 5,6-epoxy-1,2,6-trimethyl-tricyclo-[5,3,2,0^{2,7}]dodecane (hereinafter "Compound (I)") comprising treating 1,2,6-trimethyltricyclo[5,3,2,0^{2,7}]dodeca-5-ene (hereinafter "Compound (II)") with a peracid.

BRIEF DESCRIPTION OF THE ACCOMPANYING DRAWINGS

DETAILED DESCRIPTION OF THE INVENTION

Figure 1:
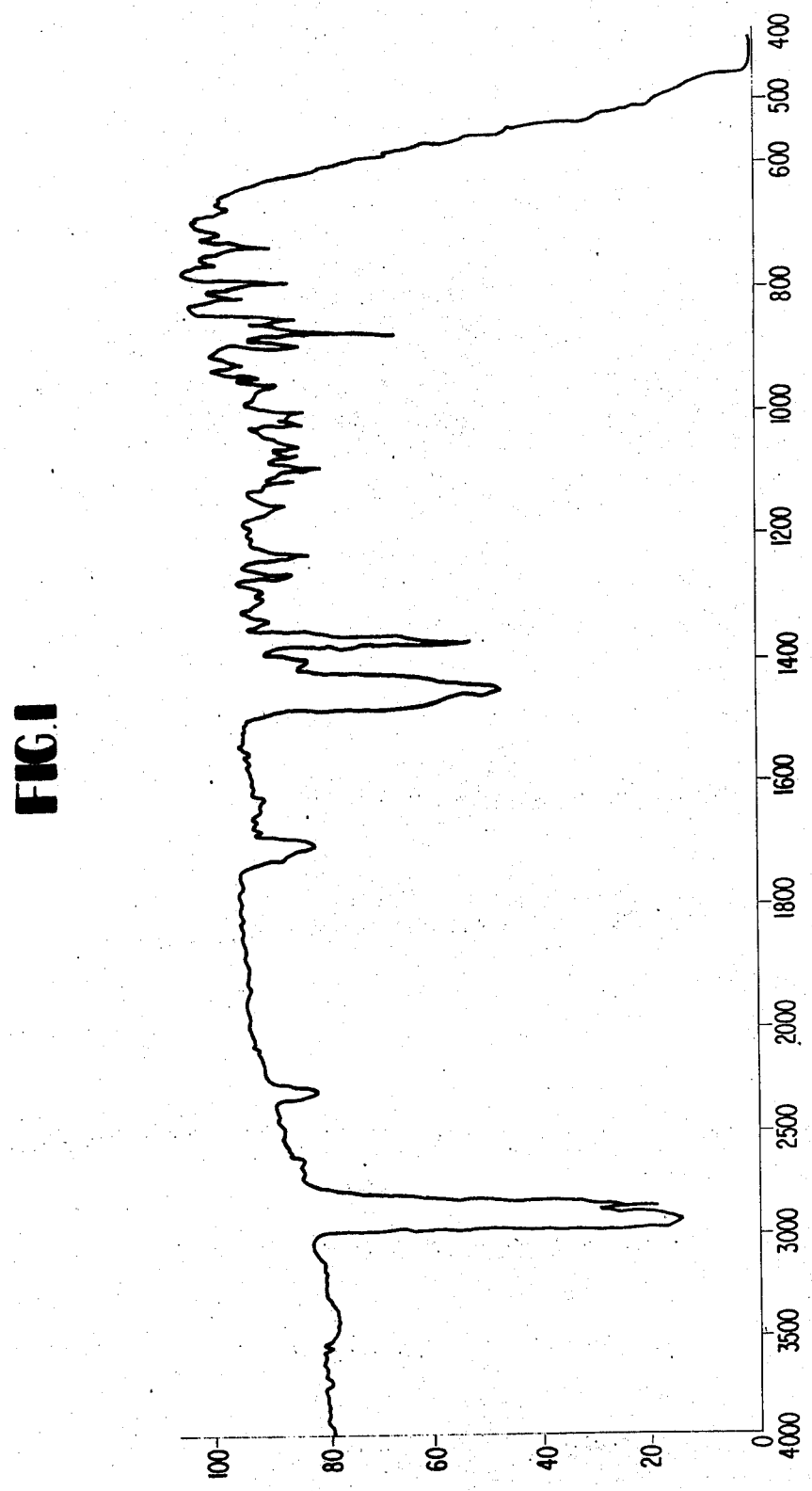
FIG. 1 is an infrared spectrum of Compound (I) obtained according to the present invention.
Figure 2:
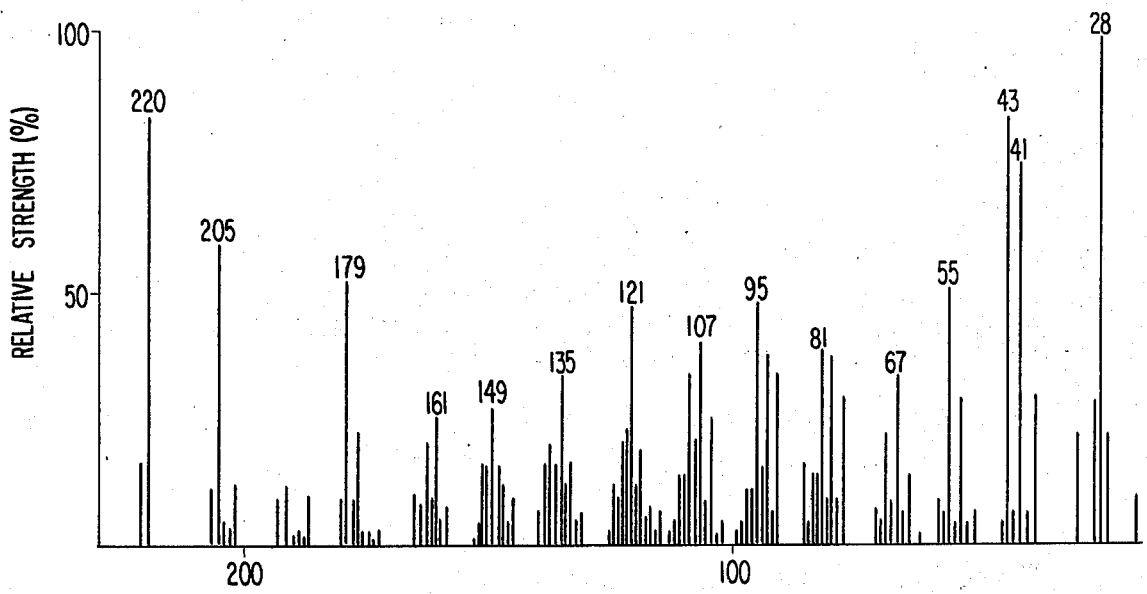
FIG. 2 is a mass spectrum of Compound (I) obtained according to the present invention.

Compound (I) produced according to the present invention is a sequiterpene compound having the molecular formula, $C_{15}H_{24}O$, and a structure represented by the formula (I).

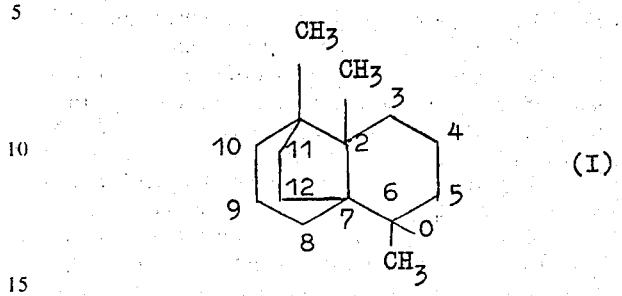

According to this invention, Compound (I) can be obtained much more cheaply than conventional amber-like fragrant substances, and is also of industrial value because of its excellent amber-like fragrance.

According to the present invention, Compound (I) can be prepared by reacting one mole of Compound (II) with about 1 to 1.2 moles of a peracid. Examples of suitable peracids which can be used include peracetic acid, perbenzoic acid, perpropionic acid, performic acid, monoperphthalic acid, trifluoroperacetic acid, etc.

The reaction can be conducted in the absence of a solvent, but proceeds more smoothly when a solvent which is inert to the peracid employed such as dichloromethane, chloroform, acetone, methyl ethyl ketone, ethyl acetate, ethyl propionate, etc., is used. Since acids are formed as the epoxidation reaction progresses, it is desirable to add a neutralizing agent to the reaction system from the beginning or during the course of the reaction or after the completion of the reaction in order to neutralize the acids formed. Suitable examples of neutralizing agents which can be employed are the carbonates or acetates of alkali metals such as sodium and potassium and hydroxides of alkaline earth metals such as calcium and barium. The reaction temperature can range from about −5° to about 10°C, preferably 0° to 5°C. The reaction can sufficiently be completed within about 8 hours, and, for example, the reaction proceeds quantitatively in the preferred temperature range as described above and is completed in about 5 hours in this temperature range.

After completion of the reaction, Compound (I) is extracted with a solvent such as dichloromethane, chloroform, etc., and the resulting extract is distilled under reduced pressure, whereby Compound (I) can be obtained in high yield. Compound (II) used as the starting material in the process can be obtained by subjecting 1,5,9-trimethylcyclododecatriene-1,5,9 (hereinafter 1,5,9-TMCDT) which is a cyclic trimer of isoprene to an intramolecular ring closure reaction with an acid catalyst as disclosed in copending U.S. Pat. application Ser. No. 537,004, filed Dec. 27, 1974 filed simultaneously herewith.

Compound (I) is a fragrant substance having a rich natural ambergris-like fragrance and a mystic peculiar wood-like odor reminiscent of a sunshing forest or moist earth, that is, a so called "natural odor" at the same time. When Compound (I) is absorbed in, e.g., filter paper and allowed to stand in a room at room temperature (e.g., about 20°–30°C), the residual fragrance is found to be very strong and to last for over one week. The fragrant odor of Compound (I) is also strong, and even when Compound (I) is diluted with ethyl alcohol, the average person even can perceive Compound (I) even at a one-tenthousandths dilution.

The utility value and application range of compound (I) of this invention are wide as a perfumery material. That is, Compound (I) can be widely used as a perfume, for example, as a component for a rich perfume to a perfume for a relatively inexpensive soap, by utilizing its residual fragrance and economy. It is possible to use Compound (I) together with rich natural amber or musk civet, or as a substitute therefor, by utilizing its ambergris-like fragrance, or together with natural sandalwood oil, or vetiver oil, or as a substitute therefor by utilizing its wood-like fragrance, thereby providing a dry and masculine rough scent necessary for a man's perfume.

Now, the present invention will be described in detail, by reference to the following Reference Example, Examples and drawings. The examples are merely illustrative and are not to be construed as limiting the scope of the present invention. Unless otherwise indicated, all parts, percents, ratios and the like are by weight.

REFERENCE EXAMPLE

In a 1*l* three-necked flask were charged 150 g of 1,5,9-trimethylcyclododecatriene-1,5,9 (melting point: 91°–92°C), 260 ml of formic acid and 150 ml of dichloromethane, and the materials were mixed. The mixture was then maintained at a temperature of 5° to 10°C. Subsequently, a mixed solution of 7.5 ml of sulfuric acid and 40 ml of formic acid was added dropwise thereto over a period of 30 minutes at 5° to 10°C, and the materials were reacted with stirring at that temperature for 3 hours, and further reacted with stirring at room temperature (i.e., about 20° to 30°C) for 3 additional hours. After completion of the reaction, dichloromethane was recovered by distillation, and then formic acid was distilled off water under reduced pressure. Subsequently, the residue was neutralized and washed with a 3% aqueous sodium bicarbonate solution, washed with water, and dried with anhydrous sodium sulfate, followed by distillation in vacuo at 75°–80°C/0.05 mmHg, whereby 135 g of the fraction of Compound (II) was obtained.

As a result of the IR, NMR, and MAS spectra of Compound (I) and also as a result of X-ray crystal structural analysis of a crystalline ketone compound derived from Compound (II), Compound (II) was determined to have the following structural formula (II).

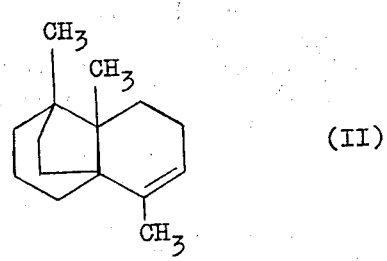

(II)

EXAMPLE 1

A mixture of 20.4 g (0.1 mole) of Compound (II) and 17 g of sodium carbonate was added to 100 ml of dichloromethane, with stirring. 20.8 g (0.11 mole) of an acetic acid solution containing 40% peracetic acid was added dropwise thereto over a period of 2 hours, while maintaining the solution at 0° to 5°C. The solution was then stirred at that temperature for 2 hours, and further stirred at room temperature for 3 additional hours. Subsequently, the resulting solution was mixed with 200 ml of water and extracted twice with dichloromethane. The extract was washed with an aqueous saturated sodium chloride solution until the extract became neutral, and then dried with anhydrous sodium sulfate. Subsequently, dichloromethane was recovered by distillation, and the residue was then distilled in vacuum, whereby 21 g of an oily fraction having a boiling point of 85°–90°C/0.3 mmHg) was obtained in a yield of 95%.

| Refractive Index: | $n_D^{25}$ | 1.5063 | |
|---|---|---|---|
| Elemental Analysis: | | C | H |
| Calculated (%): | | 81.76 | 10.98 |
| Found (%): | | 81.65 | 11.09 |
| IR Spectrum: | Epoxide characteristic absorption: 802 cm⁻¹, 880 cm⁻¹, 1240 cm⁻¹ | | |
| MAS Spectrum: | M⁺ 220 (molecular ion) | | |
| NMR Spectrum: | | | |

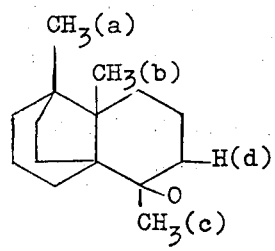

a. 0.72 ppm (3H, s)
b. 0.75 ppm (3H, s)
c. 1.18 ppm (3H, s)
d. 2.87 ppm (1H, t)

Compound (I) was isomerized with a Lewis acid, using the procedures as disclosed in copending U.S. Pat. application Ser. No. 537,005, filed Dec. 27, 1974, filed simultaneously herewith, whereby a crystalline ketone compound (melting point: 99.5°–100.5°C) was obtained. The structure of the ketone compound thus obtained was directly determined by X-ray crystal structural analysis.

| X-ray Crystal Structural Analysis of the Ketone Compound: | | | |
|---|---|---|---|
| Lattice constant: | a=7.975A, | b=13.225A, | c=7.147A |
| | α=95.7°, | β=60.0°, | γ=104.2° |
| Space group: | P1̄, Z=2 | | |
| Values (A) of X, Y and Z as solid coordinates: | | | |
| Atom | RX | RY | RZ |
| C1 | 0.9791 | 5.7703 | 1.7584 |
| C2 | 2.3424 | 5.6967 | 2.4672 |
| C3 | 3.1955 | 4.4961 | 2.0121 |
| C4 | 2.3586 | 3.2151 | 1.9691 |
| C5 | 3.0098 | 1.9672 | 1.2955 |
| C6 | 3.6074 | 2.3334 | −0.0927 |
| C7 | 2.4712 | 2.8519 | −1.0345 |
| C8 | 1.5720 | 3.8637 | −0.3559 |
| C9 | 1.1293 | 3.4170 | 1.0436 |
| C10 | 0.2013 | 4.4893 | 1.6283 |
| C11 | 0.5477 | 1.9829 | 0.9738 |
| C12 | 1.7833 | 1.0214 | 1.1082 |
| C13 | −1.1340 | 4.7008 | 0.8295 |
| C14 | 1.9438 | 2.8689 | 3.4240 |
| C15 | 4.1078 | 1.2928 | 2.1657 |

-continued

| | | | |
|---|---|---|---|
| O1 | 0.5492 | 6.8548 | 1.4110 |

Bonding angle among atoms from the solid coordinates:

| Three Atoms | Bonding Angle (degree) |
|---|---|
| C2-C1-C10 | 117.21 |
| C1-C2-C3 | 113.06 |
| C3-C4-C9 | 109.94 |
| C5-C4-C14 | 109.74 |
| C4-C5-C12 | 102.04 |
| C6-C5-C15 | 109.29 |
| C6-C7-C8 | 112.52 |
| C4-C9-C10 | 110.05 |
| C8-C9-C11 | 109.68 |
| C1-C-10-C13 | 111.65 |
| C5-C12-C11 | 104.92 |
| C2-C1-O1 | 119.15 |
| C2-C3-C4 | 110.94 |
| C3-C4-C14 | 107.85 |
| C9-C4-C14 | 112.11 |
| C4-C5-C15 | 113.57 |
| C12-C5-C15 | 111.06 |
| C7-C8-C9 | 112.68 |
| C4-C9-C11 | 101.76 |
| C10-C9-C11 | 115.93 |
| C9-C10-C13 | 114.50 |
| C10-C1-O1 | 123.46 |
| C3-C4-C5 | 116.95 |
| C5-C4-C9 | 100.20 |
| C4-C5-C6 | 110.94 |
| C6-C5-C12 | 109.74 |
| C5-C6-C7 | 109.65 |
| C4-C9-C8 | 110.69 |
| C8-C9-C10 | 108.58 |
| C1-C10-C9 | 108.39 |
| C9-C11-C12 | 105.50 |

Figure 4:
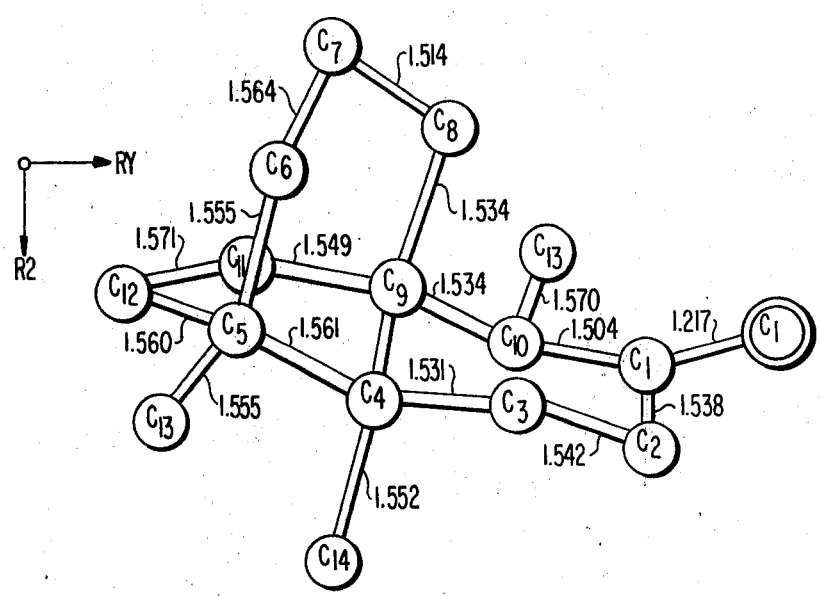
FIG. 4 shows the stereostructural form of a ketone compound obtained by isomerization of Compound (I).
Figure 3:
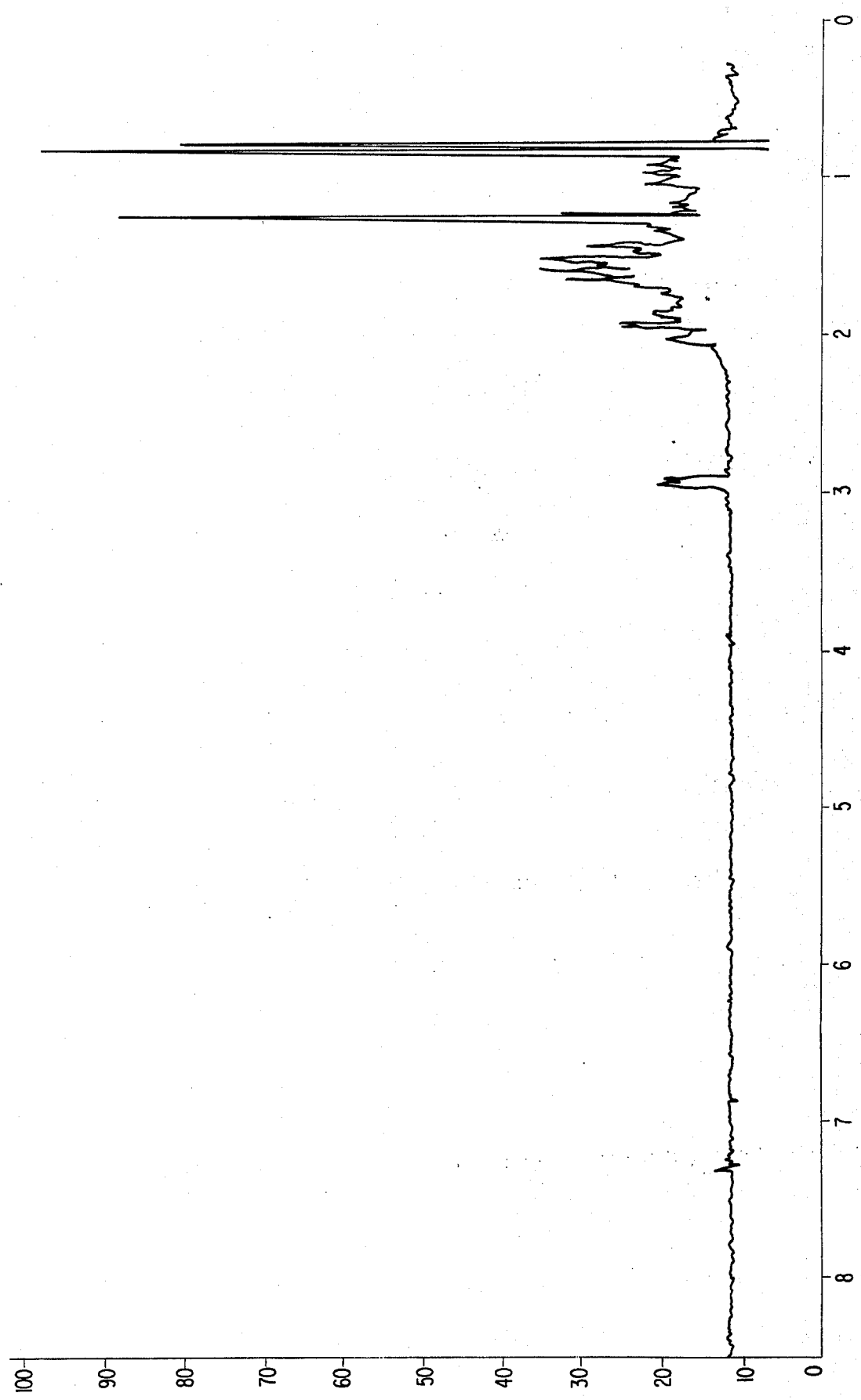
FIG. 3 is an NMR spectrum of Compound (I) obtained according to the present invention.

The stereostructural formula shown in FIG. 4 can be derived from these values.

Molecular Formula: $C_{15}H_{24}O$

As a result, the ketone compound was determined to have the stereostructural formula (III):

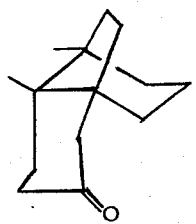

(III)

From the foregoing result, the stereostructure of Compound (I) of the present invention was determined to be the formula (IV):

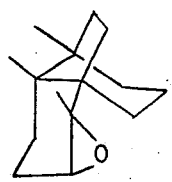

(IV)

EXAMPLE 2

The reaction was carried out under the same conditions as directed in Example 1, except that a dichloromethane solution containing 15 g (0.11 mole) of perbenzoic acid in place of the acetic acid solution containing 40% peracetic acid and 5.8 g of sodium carbonate were used, whereby Compound (I) was obtained in a yield of 93%.

EXAMPLE 3

The following formulation is suitable as a base for a perfume or an eau-de-cologne:

| | g |
|---|---|
| Vetiveryl Acetate | 80 |
| Patchouli Oil | 150 |
| Oak Moth | 50 |
| Musk Ketone | 20 |
| Coumarin | 10 |
| Methyl Ionone | 80 |
| Ionone | 10 |
| Hydroxycitronellal | 90 |
| Cinnamic Alcohol | 30 |
| Stearyl Acetate | 25 |
| Phenylethyl Alcohol | 40 |
| Geraniol | 50 |
| Terpineol | 15 |
| Galbanum Oil | 10 |
| Lavender Oil | 20 |
| Bergamot Oil | 30 |
| Ylang-ylang Oil | 20 |
| Compound (I) | 70 |
| | 800 g |

EXAMPLE 4

The following formulation is suitable for a soap perfumery.

| | g |
|---|---|
| Oak Moth Resinoid | 50 |
| Cabdanum | 20 |
| Patchouli Oil | 50 |
| Heliotropine | 120 |
| Musk Ambrette | 150 |
| Vanillin | 50 |
| Benzyl Salicylate | 60 |
| Amyl Salicylate | 240 |
| Geranium Oil | 70 |
| Geraniol | 30 |
| Anisic Aldehyde | 60 |
| Lavandine Oil | 60 |
| Compound (I) | 40 |
| | 1000 g |

While the invention has been described in detail and with reference to specific embodiments thereof, it will be apparent to one skilled in the art that various changes and modifications can be made therein without departing from the spirit and scope thereof.

What is claimed is:

1. 5,6-Epoxy-1,2,6-trimethyltricyclo[5,3,2,0$^{2,7}$]dodecane having the formula (I)

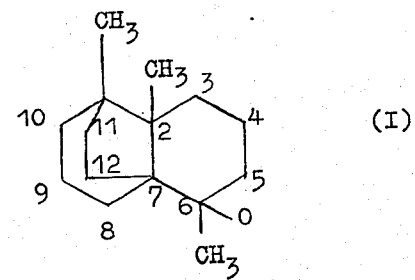

(I)

2. A perfume composition having an amber-like odor comprising an olfactory amount of 5,6-epoxy-1,2,6-trimethyltricyclo[5,3,2,0$^{2,7}$]dodecane according to claim 1.

* * * * *